United States Patent
Commereuc

[11] Patent Number: 5,898,092
[45] Date of Patent: *Apr. 27, 1999

[54] SUPPORTED CATALYST CONTAINING RHENIUM AND ALUMINUM PROCESS FOR THE PREPARATION THEREOF AND USE FOR THE METATHESIS OF OLEFINS

[75] Inventor: Dominique Commereuc, Meudon, France

[73] Assignee: Institut Français du Pétrole, France

[*] Notice: This patent is subject to a terminal disclaimer.

[21] Appl. No.: 08/862,698

[22] Filed: May 23, 1997

Related U.S. Application Data

[63] Continuation of application No. 08/799,080, Feb. 11, 1997, abandoned, which is a continuation of application No. 08/554,438, Nov. 6, 1995, abandoned.

[30] Foreign Application Priority Data

Oct. 20, 1995 [FR] France .................. 95 12335

[51] Int. Cl.⁶ .............. C07C 6/02; B01J 31/14; B01J 31/32
[52] U.S. Cl. ............ 585/647; 585/646; 502/171; 502/172
[58] Field of Search ............ 502/102, 172, 502/355, 170, 171; 585/646, 647

[56] References Cited

U.S. PATENT DOCUMENTS

| | | | |
|---|---|---|---|
| 4,454,368 | 6/1984 | Banks | 585/646 |
| 4,943,397 | 7/1990 | Johnson | 260/405.5 |
| 5,135,958 | 8/1992 | Radlowski et al. | 518/728 |
| 5,218,131 | 6/1993 | Warwel et al. | 554/63 |
| 5,342,985 | 8/1994 | Herrmann et al. | 556/482 |
| 5,405,924 | 4/1995 | Kelsey | 526/142 |
| 5,449,852 | 9/1995 | Chauvin et al. | 585/647 |
| 5,596,115 | 1/1997 | Commereuc | 556/27 |
| 5,747,408 | 5/1998 | Commereuc | 502/171 |
| 5,747,409 | 5/1998 | Commereuc | 502/171 |

FOREIGN PATENT DOCUMENTS

| | | | |
|---|---|---|---|
| 313 283 | 1/1988 | European Pat. Off. | C07C 11/12 |
| 313283 | 10/1988 | European Pat. Off. | |
| 444 265 | 12/1990 | European Pat. Off. | |
| 639 549 | 8/1994 | European Pat. Off. | C07C 6/04 |

*Primary Examiner*—Michael Lewis
*Assistant Examiner*—Alexander G. Ghyka
*Attorney, Agent, or Firm*—Millen, White, Zelano, & Branigan, P.C.

[57] ABSTRACT

A supported catalyst with rhenium and also containing aluminium introduced by a compound of the formula $(OR)_qAlR'_r$ with R being a hydrocarbyl residue with from 1 to 40 carbon atoms, R' being an alkyl residue with from 1 to 20 carbon atoms, and with q and r equal to 1 or 2 with q+r=3. A process for the preparation of a catalyst comprising impregnating a compound of rhenium on a porous support formed by refractory oxides and/or alumino-silicates of an acid, neutral or basic nature, roasting at a temperature of form 200 to 950° C. and impregnating with said aluminium compound. The catalyst is used for the metathesis of olefins.

26 Claims, No Drawings

SUPPORTED CATALYST CONTAINING RHENIUM AND ALUMINUM PROCESS FOR THE PREPARATION THEREOF AND USE FOR THE METATHESIS OF OLEFINS

This application is a continuation of application Ser. No. 08/799,080, filed Feb. 11, 1997, now abandoned, which is a continuation of Ser. No. 08/554,438, filed Nov. 6, 1995, now abandoned.

BACKGROUND OF THE INVENTION

The present invention concerns a process for the preparation of a rhenium-based catalyst and the use thereof for the metathesis of olefins.

The metathesis of olefins, or a reaction for the mutual redistribution of the alkylidene groups, is of great practical interest, for example for mutual re-balancing of the light olefins which result from steam cracking such as ethylene, propylene and butenes.

Different types of catalysts can be used in the metathesis reaction, either homogeneous catalysts when the constituent elements thereof are all soluble in the medium of the reaction, or heterogeneous catalysts when at least one of the elements is insoluble in the reaction medium. The latter are particularly attractive when the active metal causes problems and it is necessary to envisage re-using same without losses. That is the case for example with rhenium-based catalysts.

There are not many rhenium-based supported catalysts which are active for the reaction for the metathesis of olefins. The oldest and most generally used is rhenium heptoxide deposited on inorganic oxides, in most cases alumina (British patent No. 1,954,864, British Petroleum Co Ltd, 1964), but also on supports comprising both alumina and another co-oxide (R Nakamura, Rec Trav Chim Pays-Bas, Vol 96, 1977, page M31). The use of organometallic co-catalysts such as tetraalkyltins associated with the catalyst comprising rhenium oxide on alumina permits, amongst other advantages, the metathesis of functional olefins (J C Mol, C Boelhouwer et al., J. Chem. Soc. Chem. Comm., 1977, page 198). W. Hermann claimed the use of complexes such as methyltrioxorhenium and pentamethylcyclopentadienyltrioxorhenium which are deposited on various inorganic oxides including in particular alumina and silica-aluminas (Hoechst, European patents 373,488-A and 522,067-A).

SUMMARY OF THE INVENTION

The invention describes a preparation process for obtaining modified rhenium-based catalysts which are more active than those in the prior art and the use of those catalysts for the metathesis of olefins. It has been found in fact that the addition to a rhenium-based catalyst which is supported on an inorganic porous support and roasted at a temperature of from 200 to 1000° C., of at least one particular compound of aluminium, unexpectedly improves the activity of such catalysts, making it possible, for an identical level of activity, to use smaller proportions of rhenium, which is important having regard to the cost of that metal.

The general formula of the particular aluminium compound is $(RO)_q AlR'_r$ wherein R is a hydrocarbyl residue containing from 1 to 40 carbon atoms, R' is an alkyl residue containing from 1 to 20 carbon atoms, and q and r are equal to 1 or 2 in such a way that the sum q+r is equal to 3.

The rhenium-based catalyst according to the invention comprises at least three components: at least one inorganic porous support, from 0.01 to 20% by weight of rhenium (expressed as metal) in oxide form, and from 0.01 to 10% by weight of aluminium introduced in the form of the aluminium compound of the general formula $(RO)_q AlR'_r$.

The invention also concerns processes for preparation of the catalyst. More precisely, in a preparation process according to the invention, there is prepared a roasted catalyst precursor containing at least one inorganic porous support and the rhenium, and then said precursor is brought into contact with a compound $(RO)_q AlR'_r$.

The roasted catalyst precursor is obtained by introducing at least one precursor of rhenium on the support or supports, and then roasting.

The inorganic porous support is selected from the group formed by refractory oxides and/or alumino-silicates which may be of an acid, neutral or basic nature. By way of example, and without this list being limitative, mention may be made of the following: alumina, silica, silica-aluminas, zeolites, titanium oxide, zirconia, niobium oxide, chromium oxide, magnesia and tin oxide.

The support used is advantageously an inorganic support of acid or neutral character, more particularly an alumina, a silica or a silica-alumina, with a specific surface area of from 10 to 400 m²/g. Preferably the porous support is selected from the group formed by alumina or by a compound containing at least 75% by weight of alumina, which is advantageously to be of an appreciable surface area, for example at least 10 m²/g and preferably at least 50 m²/g, and an adequate volume of pores, for example at least 0.1 ml/g and preferably 0.3–1 ml/g. It is possible to use for example an alumina of the same type as those of catalytic reforming catalysts.

The precursor of the rhenium compound used is preferably selected from the group formed by rhenium heptoxide, ammonium perrhenate and perrhenic acid. The compound of rhenium can be introduced on the support for example by sublimation in the vapor phase or by impregnation in solution. It is preferred generally to use the dry impregnation method in which the rhenium compound is dissolved in water or in an organic solvent, for example a hydrocarbon, an alcohol or an ether. The amount of rhenium on the support is regulated by the choice of the level of concentration of the impregnation solution, its amount being such that the volume of that solution is equal to or slightly less than the porous volume of the solid to be impregnated. When the amount of rhenium which is to be impregnated is greater than that which a solution makes it possible to introduce, at its saturation limit, the operation has to be effected a number of times, with intermediate drying operations, to remove the impregnation solvent, at a temperature of for example from 90 to 250° C., preferably from 100 to 180° C. That makes it possible to introduce from 0.01 to 20%, preferably from 0.1 to 15% and still more advantageously from 0.5 to 8% by weight of rhenium (expressed as rhenium metal).

After the rhenium precursor has been introduced on to the support, drying is effected at a temperature of for example from 90 to 250° C., preferably from 100 to 180° C., followed by roasting at a temperature of from 200 to 1000° C., for example from 250 to 1000° C. and preferably from 300 to 600° C., for a period of from 10 minutes to 10 hours and preferably for from 30 minutes to 5 hours. After roasting the solid is cooled in a dry inert atmosphere, for example in nitrogen or argon.

Any existing support which is loaded with rhenium oxide is suitable and any mode of preparation is acceptable. Rhenium-based catalysts which are commercially available at the present time may also be suitable.

The aluminium compound corresponds to the general formula $(RO)_q AlR'_r$ wherein R is a hydrocarbyl residue containing from 1 to 40 carbon atoms, for example alkyl, cycloalkyl, alkenyl, aryl, aryl or cycloalkyl which are substituted, preferably a hydrocarbyl residue with from 2 to 30 carbon atoms, which residue can be substituted by at least one alkoxy group or at least one halogen. By way of example, and without the following list being limitative, R may be an ethyl, n-propyl, isopropyl, n-butyl, t-butyl, cyclohexyl, benzyl, diphenylmethyl, phenyl, 2-methylphenyl, 4-methylphenyl, 2-methoxyphenyl, 4-methoxyphenyl, 2,6-dimethylphenyl, 2,6-diisopropylphenyl, 2-t-butylphenyl, 2-t-butyl-4-methylphenyl, 2,6-di-t-butylphenyl, 2,6-di-t-butyl-4-methylphenyl, 2,4,6-tri-t-butylphenyl, 2-phenylphenyl, 2,6-diphenylphenyl, 2-fluorophenyl, 4-fluorophenyl and pentafluorophenyl residue. R' is an alkyl residue containing from 1 to 20 carbon atoms, preferably from 1 to 6 carbon atoms, for example methyl, ethyl, isobutyl, and q and r are equal to 1 or 2 in such a way that the sum q+r is equal to 3.

Preparation of the compound $(RO)_q AlR'_r$ is known in the literature. Any process for the preparation of that compound is suitable. It is possible for example to react an alcohol or a phenol ROH with a trialkylaluminium $AlR'_3$ in an organic solvent, for example a hydrocarbon or an ether.

The compound of aluminium may be introduced on to the support by any of the methods known to the man skilled in the art, but it is imperative to operate in such a way as to be protected from air and moisture. The support can be impregnated with an excess of a solution containing the aluminium compound $(RO)_q AlR'_r$. After a contact time which can range from a few minutes to a few days, the solid is dried without heating and it is washed with the solvent to remove the portion of the compound which is not fixed. It is also possible, in the mode of operation which is preferred, to use the dry impregnation method. The concentration of aluminium in the solution is then adjusted in dependence on the amount of aluminium which is to be deposited on the solid in such a way that the volume of said solution is equal to or slightly less than the porous volume of the solid to be impregnated. The solvent used in the impregnation operation is preferably an organic solvent, for example a hydrocarbon or an ether. That makes it possible to introduce from 0.01 to 10%, preferably from 0.05 to 5%, and still more advantageously from 0.1 to 5% by weight of aluminium (expressed as aluminium metal).

After introduction of the aluminium compound preparation of the catalyst can be terminated by a drying operation, under vacuum or in a flow of gas which is preferably inert, at a temperature of from 0 to 1000° C., advantageously lower than 200° C. and even 0 to 180° C., preferably at a temperature close to ambient temperature of from 0 to 50° C. No chemical or thermal activation operation is necessary to initiate activity of such catalysts and the roasting operation is recommended against. It is sufficient for them to be brought into contact with an olefin for the metathesis reaction to start.

Instead of preparing the compound $(RO)_q AlR'_r$ and bringing it into contact with the supported rhenium catalyst, as described above, it is possible to bring the supported rhenium catalyst directly into contact with the precursor reactants of the compound $(RO)_q AlR'_r$ which are for example ROH and $AlR'_3$, with R and R' as defined above. In the same manner as before the preparation operation can be terminated by a drying step.

Addition of the compound $(RO)_q AlR'_r$ or its precursors to the supported rhenium catalyst may thus advantageously take place in situ in the reaction reactor, prior to the reaction, or ex situ and the modified catalyst is directly loaded into the reactor for the reaction. In the former case (in situ) it is also possible to introduce the compound or its precursors with the charge to be treated.

The invention also concerns a process for the metathesis of olefins in the presence of the above-defined catalyst at a temperature of from 20 to +200° C., preferably from 0 to +100° C., under pressure conditions which are variable depending on whether the reaction is to be conducted in the gaseous phase or in the liquid phase.

In an operation in the liquid phase the pressure is to be sufficient for the reactants and the solvent if provided to be maintained at least in respect of the majority thereof (more than 50%) in the liquid phase (or in a condensed phase). The catalyst can then be used either in the pure olefin (or olefins), or in the presence of a solvent formed by an aliphatic, cycloaliphatic or aromatic hydrocarbon, a halogenated hydrocarbon or a nitro derivative. A hydrocarbon or a halogenated hydrocarbon are preferably used.

The olefins which are capable of a metathesis reaction are monoolefins having from 2 to 30 carbon atoms, for example ethylene, propylene, butenes and pentenes, cycloolefins having from 3 to 20 carbon atoms, for example cyclopentene, cyclooctene and norbornene, polyolefins having from 4 to 30 carbon atoms, for example hexa-1,4-diene, octa-1,7-diene, and cyclopolyolefins having from 5 to 30 carbon atoms, for example cycloocta-1,5-diene, norbornadiene and dicyclopentadiene.

Other olefins which are capable of being metathesised are monoolefins or polyolefins, which are in straight-chain or ring form, bearing functional groups such as for example halogens or ester groups such as methyl oleate. The process may also use in a co-metathesis operation a mixture of the foregoing olefins.

EXAMPLES

The following Examples illustrate the invention without limiting the scope thereof.

Example 1

Preparation of the catalyst:

In a first step, a cubic gamma alumina having a specific surface area of 184 $m^2/g$ and of a porous volume of 0.67 ml/g is roasted at 300° C. in air. After cooling to ambient temperature 10 g of roasted alumina is taken off. The next step is to prepare a solution for impregnation of the rhenium by diluting 0.24 ml of a concentrated aqueous solution of perrhenic acid containing 54% by weight of rhenium (specific weight: 2.4 g/ml in 5 ml of water. That solution is impregnated on to the 10 g of alumina taken off. After 30 minutes of contact at ambient temperature the solid obtained is dried in a drying oven at 120° C. for one night. It is then roasted in a flow of air (about 20 l/h) which is dried by being passed through a molecular sieve bed at a temperature of 550° C. for a period of 2 hours. During the further cooling period a flow of dry nitrogen is substituted for the flow of air. The solution obtained is preserved and handled in an atmosphere of dry nitrogen. Its rhenium metal content is 3% by weight.

Using a 250 ml balloon flask disposed in an argon atmosphere and provided with a magnetic stirrer rod, a solution of 0.493 g of triisobutylaluminium in 20 ml of pentane is introduced, and then a solution of 1.095 g of 2,6-di-t-butyl-4-methylphenol in 30 ml of pentane is introduced dropwise with agitation and at ambient temperature.

After about 30 hours of reaction the pentane is evaporated under vacuum and analysis of the white solid remaining indicates that it is formed essentially by bis-(2,6-di-t-butyl-4-methylphenoxy)-isobutylaluminium. That compound is put back into solution in 5 ml of heptane.

The solution in heptane of bis-(2,6-di-t-butyl-4-methylphenoxy)-isobutylaluminium is then impregnated on the solid containing the rhenium obtained in the first step. After about 30 minutes of contact the heptane which is absorbed on the solid is removed by evaporation under vacuum at ambient temperature. That gives a metathesis catalyst containing 3% by weight of rhenium and 0.67% by weight of aluminium (in addition to the aluminium included in the alumina), which is preserved in a dry and inert atmosphere before use.

Use in metathesis:

Using a reactor formed by a stainless steel tube provided with a double jacket with the circulation of water for temperature regulation purposes, the catalyst prepared above is introduced, protected from air and moisture. Liquid propylene is injected by means of a pump by way of the bottom of the reactor at a flow rate of 49.6 g/h. The temperature is regulated to 35° C. and the pressure is maintained at 3.5 MPa by means of a regulator which is disposed downstream of the reactor. Under those conditions conversion of the propylene at the discharge from the reactor is 30%, in the form of an equimolar mixture of ethylene and but-2-enes.

Example 2 (comparative)

Preparation of the catalyst:

A fresh batch of catalyst is prepared as in Example 1, except that the step of preparation of and impregnation by bis-(2,6-di-t-butyl-4-methylphenoxy)-isobutylaluminium is omitted. The rhenium impregnation step as well as the drying and roasting phase are identical to those described in Example 1. That thus gives 10 g of catalyst which is preserved in a dry and inert atmosphere before use. Its rhenium metal content is 3% by weight.

Use in metathesis:

Using the same apparatus as that described in Example 1, the 10 g of catalyst prepared above is introduced. Liquid propylene is injected by means of a pump by way of the bottom of the reactor at a flow rate of 49.6 g/h. The temperature is regulated at 35° C. and the pressure is maintained at 3.5 MPa by means of a regulator disposed downstream of the reactor. Under those conditions conversion of the propylene at the discharge from the reactor is 7.4%, in the form of an equimolar mixture of ethylene and but-2-enes.

This comparative Example shows the progress afforded by the preparation method according to the invention as regards the activity of the catalyst.

I claim:

1. A catalyst comprising at least one inorganic porous support, from 0.01 to 20% by weight of rhenium in oxide form, and from 0.01 to 10% by weight of aluminum introduced in the form of an aluminum compound of the general formula $(RO)_q AlR'_r$, wherein R is an aryl residue containing up to 40 carbon atoms, R' is an alkyl residue containing from 1 to 20 carbon atoms, and q and r are equal to 1 or 2 in such a way that the sum q+r is equal to 3.

2. A catalyst according to claim 1 wherein the inorganic porous support is alumina, silica, a silica-alumina, a zeolite, titanium oxide, zirconia, niobium oxide, chromium oxide, magnesia or tin oxide.

3. A catalyst according to claim 1 wherein the inorganic porous support is alumina or a compound containing at least 75% by weight of alumina, and has a surface area of at least 10 m$^2$/g and a pore volume of at least 0.1 ml/g.

4. A catalyst according to claim 1 wherein the aluminum compound has the formula $(RO)_q AlR'_r$ wherein R is aryl optionally substituted by at least one alkoxy group or at least one halogen.

5. A catalyst according to claim 1 wherein the compound $(RO)_q AlR'_r$ results from a reaction between the compounds ROH and AlR'$_3$.

6. A process for the preparation of a modified catalyst comprising a inorganic porous support, from 0.01 to 20% by weight of rhenium in oxide form, and from 0.01 to 10% by weight of aluminum, comprising preparing a roasted catalyst precursor containing at least one inorganic porous support and rhenium, contacting said precursor with a compound of the formula $(RO)_q AlR'_r$ wherein R is aryl of up to 40 carbon atoms, R' is an alkyl residue containing from 1 to 20 carbon atoms, and q and r are equal to 1 or 2 in such a way that q+r is equal to 3, and drying the product obtained at a temperature of less than 200° C.

7. A process for the preparation of a modified catalyst according to claim 6 wherein the compound $(RO)_q AlR'_r$ results from a reaction between a compound ROH and a compound AlR'$_3$.

8. A process for the preparation of a modified catalyst comprising an inorganic porous support, from 0.01 to 20% by weight of rhenium in oxide form, and from 0.01 to 10% by weight of aluminium, comprising preparing a roasted precursor containing the inorganic porous support and rhenium, contacting said precursor with precursor reactants of the compound of the general formula $(RO)_q AlR'_r$, wherein R is a hydrocarbyl residue containing from 1 to 40 carbon atoms, R' is an alkyl residue containing from 1 to 20 carbon atoms, and q and r are equal to 1 or 2 in such a way that q+r is equal to 3, and drying the product obtained at a temperature of less than 200° C.

9. A process for the preparation of a modified catalyst according to claim 8 wherein the precursor reactants of the compound $(RO)_q AlR'_r$ are the compounds ROH and AlR'$_3$.

10. A process according to claim 6 wherein the inorganic porous support is alumina, silica, a silica-alumina, a zeolite, titanium oxide, zirconia, niobium oxide, chromium oxide, magnesia or tin oxide.

11. A process according to claim 6 wherein the inorganic porous support is selected from the group formed by alumina and compounds containing at least 75% by weight of alumina, and has a surface area of at least 10 m$^2$/g and a pore volume of at least 0.1 ml/g.

12. A process according to claim 6, wherein the catalyst precursor is obtained by contacting the support with at least one precursor rhenium compound which is rhenium heptoxide, ammonium perrhenate or perrhenic acid.

13. A process according to claim 12 wherein, after the rhenium has been introduced on to the support, roasting is effected at a temperature of from 200 to 1000° C. for a period of from 10 minutes to 10 hours.

14. A process according to claim 6 wherein the aluminum compound has the formula $(RO)_q AlR'_r$ wherein R is aryl optionally substituted by at least one alkoxy group or at least one halogen.

15. A process for the metathesis of olefins characterised in that it operates at a temperature of from −20 to +200° C. and in the presence of a catalyst according to claim 1.

16. A process for the metathesis of olefins characterised in that it operates at a temperature of from −20 to +200° C. and in the presence of a catalyst obtained in accordance with claim 6.

17. A process according to claim 15 characterised in that it operates at between 0 and 100° C.

18. A process according to claim 15 characterised in that the olefins are selected from the group formed by monoolefins having from 2 to 30 carbon atoms, cycloolefins having from 3 to 20 carbon atoms, polyolefins having from 4 to 30 carbon atoms, cyclopolyolefins having from 5 to 30 carbon atoms, monoolefins having from 2 to 30 carbon atoms bearing functional groups selected from the group formed by halogens and ester groups, and polyolefins having from 4 to 30 carbon atoms bearing functional groups selected from the group formed by halogens and the ester groups.

19. A process according to claim 15 characterised in that the olefins are selected from the group formed by ethylene, propylene, butenes, pentenes, cyclopentene, cyclooctene, norbornene, hexa-1,4-diene, octa-1,7-diene, cycloocta-1,5-diene, norbornadiene, dicyclopentadiene and methyl oleate.

20. A process according to claim 15 characterised in that it takes place in a gaseous phase.

21. A process according to claim 15 characterised in that the reactants and the solvent if provided are at least in part in the liquid phase.

22. A catalyst according to claim 1, wherein the inorganic porous support is alumina, silica-alumina or a zeolite.

23. A process according to claim 6, wherein the inorganic porous support is alumina, silica-alumina or a zeolite.

24. A process according to claim 8, wherein the inorganic porous support is alumina, silica-alumina or a zeolite.

25. A catalyst comprising at least one inorganic porous support, from 0.01 to 20% by weight of rhenium in oxide form, and from 0.01 to 10% by weight of aluminum in the form of an aluminum compound of the general formula $(RO)_q AlR'_r$, wherein R is an aryl residue comprising up to 40 carbon atoms, R' is an alkyl residue containing from 1 to 20 carbon atoms, and q and r are equal to 1 or 2 in such a way that the sum q+r is equal to 3.

26. A catalyst according to claim 1, wherein R is benzyl, diphenylmethyl, phenyl, 2-methylphenyl, 4-methylphenyl, 2-methoxyphenyl, 4-methoxyphenyl, 2,6-dimethylphenyl, 2,6-diisopropylphenyl, 2-t-butylphenyl, 2-t-butyl-4-methylphenyl, 2,6-di-t-butylphenyl, 2,6-di-t-butyl-4-methylphenyl, 2,4,6-tri-t-butylphenyl, 2-phenylphenyl, 2,6-diphenylphenyl, 2-fluorophenyl, 4-fluorophenyl or pentafluorophenyl.

* * * * *